United States Patent [19]

Noël

[11] 4,246,272
[45] Jan. 20, 1981

[54] BENZAMIDINE DERIVATIVES

[75] Inventor: Michel Noël, Houilles, France

[73] Assignee: Aron S.A., Suresnes, France

[21] Appl. No.: 922,232

[22] Filed: Jul. 5, 1978

[30] Foreign Application Priority Data

Jul. 20, 1977 [GB] United Kingdom ............... 30523/77

[51] Int. Cl.³ .................... A61K 31/42; C07D 271/06; C07D 261/08
[52] U.S. Cl. .................................. 424/272; 548/133; 548/245; 548/246
[58] Field of Search .................... 260/307 G; 427/272; 548/133, 245, 246

Primary Examiner—Donald G. Daus
Assistant Examiner—D. B. Springer
Attorney, Agent, or Firm—Young & Thompson

[57] ABSTRACT

The invention relates to a compound selected from the group consisting of compounds of the formula:

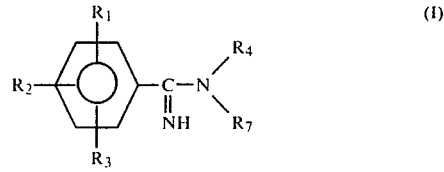

in which $R_1$, $R_2$ and $R_3$ are independently selected from hydrogen, halogen, trifluoromethyl, nitro, $C_{1-4}$ alkoxy and $C_{1-4}$ alkyl, $R_4$ represents a heterocyclic radical selected from the radicals having the formulae

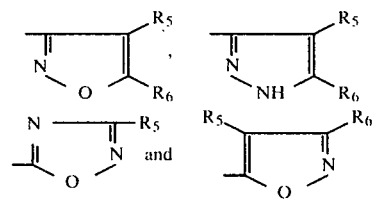

in which $R_5$ and $R_6$ are independently selected from hydrogen, $C_{1-4}$ alkyl, phenyl and halophenyl, $R_7$ is selected from hydrogen and $C_{1-4}$ alkyl, and a pharmaceutically acceptable acid addition salt thereof. These compounds are useful for the treatment of gastric ulcers.

5 Claims, No Drawings

BENZAMIDINE DERIVATIVES

This invention relates to new benzamidine derivatives, to a process for their preparation and to therapeutic compositions containing the same, particularly applicable to the treatment of gastric or duodenal ulcers.

The present invention relates to compounds of the formula:

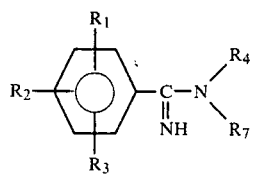

in which $R_1$, $R_2$ and $R_3$ represent independently a hydrogen atom, a halogen atom, a trifluoromethyl group, a nitro group, a $C_{1-4}$ alkoxy group or a $C_{1-4}$ alkyl group, $R_4$ represents a heterocyclic radical selected from the radicals having the formulae

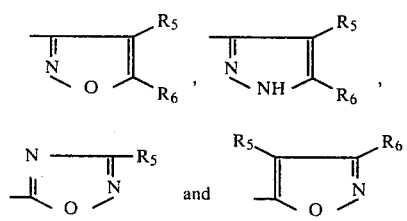

in which $R_5$ and $R_6$ represent independently a hydrogen atom, a $C_{1-4}$ alkyl group, a phenyl group or a halophenyl group, $R_7$ represents a hydrogen atom or a $C_{1-4}$ alkyl group, and their pharmaceutically acceptable acid addition salts.

The acid addition salts may typically be those formed with hydrochloric, sulfuric, phosphoric, methane sulfonic, maleic, succinic, pamoic, acetic, fumaric, lactic, aspartic, citric and chloroacetic acids.

The new compounds of this invention may be prepared according to conventional methods.

For example, the compounds in which $R_4$ is an oxadiazolyl group may be prepared according to one of the following methods comprising:

(a) reacting a benzamidine of the formula:

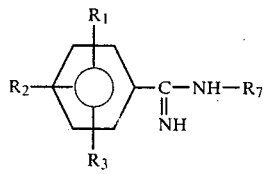

with a chloro derivative of the formula:

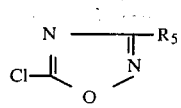

(b) reacting a benzamidine of the formula (II) with a derivative of the formula:

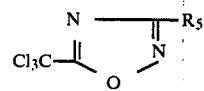

(c) reacting a benzamidine of the formula:

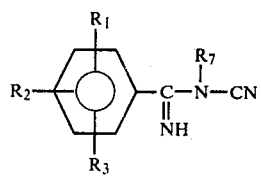

with a compound of the formula:

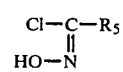

The compounds in which $R_4$ is an isoxazolyl or pyrazolyl group may be prepared according to one of the following methods, comprising:

(a) reacting a compound of the formula:

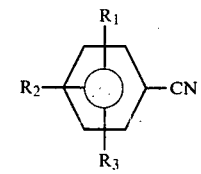

in which X represents an alkoxy or alkylthio group, with a derivative of the formula:

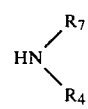

in which $R_4$ and $R_7$ have the aforesaid meanings.

(b) reacting a compound of the formula:

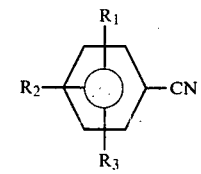

with a derivative of the formula

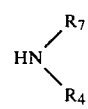

as the aryl sulfonate;

(c) reacting a derivative of the formula (VIII) with a derivative of the formula

in the presence of an alkaline agent selected from sodium, sodamide and sodium methoxide;

(d) reacting a derivative of the formula (VIII) with a derivative of the formula

in the presence of aluminum chloride.

The following non limiting Examples illustrate the preparation of compounds of the formula (I).

EXAMPLE 1

3-(Trifluoromethyl)-N-(3-phenyl-1,2,4-oxadiazol-5-yl)benzamidine

In a 500 ml flask provided with a condenser, a thermometer and a stirring device are added 22.4 g (0.1 mole) 3-trifluoromethylbenzamidine hydrochloride and 100 ml water. Complete solubilization is obtained. Methylene chloride (50 ml) followed by 10 N sodium hydroxide solution (20 ml; 0.2 mole) are then added thereto. The reaction mixture is cloudy, whitish. A solution of 18 g (0.1 mole) 3-phenyl-5-chloro-oxadiazole in 50 ml methylene chloride is then added. The temperature increases gradually to 41° C. (refluxing temperature of methylene chloride) while a white solid is produced. The reaction mixture is stirred for a further period of time of 5 hours, and is then left quiescent overnight.

The solid material is filtered off, and washed successively with water, methylene chloride and ethanol. After drying, it is recrystallized from 5 volumes Cellosolve, to give 27 g (81%) of the title compound. M.p. (cap.)=224° C.

EXAMPLE 2

N-[3-(4-chlorophenyl)-1,2,4-oxadiazol-5-yl]benzamidine

In a 500 ml flask provided with a condenser, a thermometer and a stirring device are added 15.7 g (0.13 mole) benzamidine and 40 ml acetonitrile. A solution of 38.7 g (0.13 mole) 3-(4-chlorophenyl)-5-trichloromethyl-oxadiazole in 160 ml acetonitrile is then added thereto. The temperature increases gradually to 40° C. and a white solid is found to occur. After stirring for 2 hours, the material is filtered off and washed with acetonitrile. After drying, the product is recrystallized from 6 volumes Cellosolve, to give 21 g (54%) of the title compound, M.p. (cap.): 231° C.

EXAMPLE 3

N-(3-phenyl-1,2,4-oxadiazol-5-yl)-benzamidine

In a 250 ml flask provided with a condenser, a thermometer and a stirring device are added 7.8 g (0.05 mole) benzhydroxamyl chloride, 7.3 g (0.05 mole) N-cyano-benzamidine and 100 ml ethanol. The reaction mixture is refluxed for 4 hours. The resulting solution is clear. The material crystallizes on cooling. It is filtered off and recrystallized from 15 volumes ethanol, to give 1.6 g (12%) of the title compound, M.p. (cap.) 184° C.

EXAMPLE 4

N-(5-methyl-isoxazol-3-yl)benzamidine)

In a 1 liter flask provided with a condenser, a thermometer and a stirring device are added 93 g (0.5 mole) ethyl benzamidate as the hydrochloride, 74 g (0.75 mole) 3-amino-5-methyl isoxazole and 800 ml ethanol. A clear solution is obtained. The solution is warmed to maintain the temperature at 35° C. during a period of time of 8 hours. The solvent is removed under reduced pressure and the residue is taken up into 400 ml isopropanol. The insoluble is removed. The filtrate crystallizes on cooling. The resulting solid material is filtered off, dissolved in 120 ml distilled water and made alkaline with concentrated sodium hydroxide. The resulting crystalline solid material is filtered off and recrystallized from isopropanol, to give 14 g (14%) of the title compound, M.p. (cap.): 127°–129° C.

EXAMPLE 5

N-(5-methyl-isoxazol-3-yl)-benzamidine

In a 1 liter flask provided with a condenser, a thermometer and a stirring device are added 250 ml acetonitrile, 24.5 g 3-amino-5-methyl-isoxazole. This gives a solution to which are added 54 g propyl thiobenzimidate hydrochloride, and the resulting suspension is then refluxed. Dissolution is found to occur. Refluxing is maintained 2 hours. The material crystallizes and is left aside overnight, after which it is filtered, suction filtered and dried. Crystallization from isopropanol and reconversion to the base by addition of the suitable amount of sodium hydroxide solution give 28 g N-(5-methyl-isoxazol-3-yl)-benzamidine. (Yield: 56%). M.p. (capillary tube): 127°–129° C.

EXAMPLE 6

N-(3,4-dimethyl-isoxazol-5-yl)benzamidine

In a 250 ml flask provided with a condenser, a thermometer and a stirring device are added 10.3 g (0.1 mole) benzonitrile, 11.2 g (0.1 mole) 5-amino-3,4-dimethyl-isoxazole and 100 ml anhydrous benzene.

The reaction mixture is heated at 60° C. and 2.3 g (0.1 g-at.) sodium dispersed in paraffin are added thereto. An exothermal reaction is found to occur, with substantial foaming. Refluxing is maintained 2 hours. After cooling, the benzene is removed under reduced pressure. The oily residue is taken up into 5 volumes ethanol. The resulting solution is treated with carbon black and filtered.

The ethanol is removed under reduced pressure, the resulting residue is taken up into a small amount of water, after which it is filtered off and dried, to give 3.5 g (16%) N-(3,4-dimethylisoxazol-5-yl)-benzamidine, m.p. (cap.) 122°–124° C.

The characteristics of the compounds prepared in Examples 1–6 together with those of other compounds prepared in an analogous manner are set forth in Table I.

TABLE I

| Compound n° | Formula | M.p.(cap.) °C. |
|---|---|---|
| 1 | C₆H₅–C(=NH)–NH–N=CH–CH=C(CH₃)–O (isoxazole, 5-CH₃) | 127–129 |
| 2 | 4-Cl-C₆H₄–C(=NH)–NH–N=CH–CH=C(CH₃)–O (isoxazole, 5-CH₃) | 165–166 |
| 3 | 3,4-(CH₃O)₂-C₆H₃–C(=NH)–NH–N=CH–CH=C(CH₃)–O (isoxazole, 5-CH₃), HCl | 246 |
| 4 | 3-CF₃-C₆H₄–C(=NH)–NH–N=CH–CH=C(CH₃)–O (isoxazole, 5-CH₃) | 103–104 |
| 5 | C₆H₅–C(=NH)–NH–N=CH–O–CH=C(CH₃) (isoxazole, 4-CH₃), HCl | 225–227 |
| 6 | C₆H₅–C(=NH)–NH–N=CH–NH–C(CH₃)=CH (pyrazole, 5-CH₃), HCl | 248–250 |
| 7 | C₆H₅–C(=NH)–NH–C(=N–O–)=C(CH₃)–N (1,2,4-oxadiazole, 5-CH₃) | 168–169 |
| 8 | C₆H₅–C(=NH)–NH–C(=N–O–)=N–C₆H₅ (1,2,4-oxadiazole, 5-C₆H₅) | 184 |
| 9 | C₆H₅–C(=NH)–NH–C(=N–O–)=N–C₆H₄-4-Cl | 231 |
| 10 | 4-Cl-C₆H₄–C(=NH)–NH–C(=N–O–)=N–C₆H₅ | 237 |
| 11 | 3-CF₃-C₆H₄–C(=NH)–NH–C(=N–O–)=N–C₆H₅ | 224 |

TABLE I-continued

| Compound n° | Formula | M.p.(cap.) °C. |
|---|---|---|
| 12 | [structure: phenyl with NO2, C(=NH)-NH-C(=N-O-)- phenyl] | 249–251 |
| 13 | [structure: phenyl-C(=NH)-NH- linked to 3,5-dimethylisoxazole] | 122–124 |

On pharmacological investigation, the compounds tested exhibited an activity against experimentally induced ulcer models induced by phenylbutazone, acetylsalicylic acid, Polymyxine B, against stress ulcer and against Shay's ulcer.

A comparative investigation was conducted on three of said models.

Phenylbutazone induced ulcer

Male Sprague Dawley rats weighing about 350 g, which had been kept fasting 24 hours prior to the test, were administered orally 150 mg/kg phenylbutazone. One hour prior to phenylbutazone administration, the animals were treated with the test compound, by the oral route. The animals are sacrificed after 18 hours. The results obtained are expressed as percent protection with respect to the reference group.

Acetylsalicylic acid induced ulcer

200–250 g rats, which had been kept fasting during 24 hours, are orally administered 100 mg/kg acetylsalicylic acid, and are sacrificed after 4 hours. The test compound is administered as disclosed above, and the results obtained are expressed in an analogous manner.

Polymyxine B induced ulcer

Male 200–250 g Wistar rats, kept fasting 24 hours prior to the test, are sub-cutaneously administered 7.5 mg/kg Polymyxine B and are sacrificed 2 hours later. The test compound is administered as previously described, intraperitoneally or orally, 1 hour prior to the ulcer-producing agent.

Results are given in Table II. The test compounds are administered at a dosage of 100 mg/kg. The results are scored according to the following scale:

1: in excess of 10% protection with respect to the reference group
2: in excess of 25% protection with respect to the reference group
3: in excess of 40% protection with respect to the reference group
4: in excess of 60% protection with respect to the reference group

TABLE II

| Compound n° | Test compounds administered at a dosage of 100 mg/kg, p.o. or i.p. Protection against ulcers induced by | | |
|---|---|---|---|
| | Phenylbutazone | Acetylsalicylic acid | Polymyxine B |
| 1 | 3 | 4 | 4 |
| 2 | — | 1 | 2 |
| 7 | 1 | 3 | 1 |
| 8 | 4 | 3 | 3 |
| 10 | 3 | 3 | 1 |
| 11 | 3 | 3 | 3 |
| 12 | 4 | 4 | 3 |

It should be noted that, for said compounds, optimal results sometimes appear at dosages below or in excess of 100 mg/kg, said mean dosage being given solely for comparative purposes.

The acetylsalicylic acid introduced ulcer model was used to investigate the influence on activity of the dosage administered. The results obtained are given in Table III and are expressed as percent protection with respect to the control group.

TABLE III

| Compound n° | Dosage administered, per os (mg/kg) | | | | | |
|---|---|---|---|---|---|---|
| | 25 | 50 | 75 | 100 | 150 | 300 |
| 1 | 42 | — | 72 | — | 78.5 | — |
| 8 | — | 30 | — | 51 | — | 60 |
| 11 | — | 15 | 29 | 46.5 | — | 52 |
| 12 | — | 28 | 47 | — | 68 | — |

No atropine-like, parasympatholytic action—the drawbacks of which are well known in human medicine—was noted with the compounds tested. Gastric acidity remained unchanged. In contrast, a stimulation of the gastric mucus which protects the gastric wall is apparent; in most cases, it is visible already on macroscopic examination.

This action was confirmed by the histological and histochemical examination. For Example:

Compound No. 8, at dosages of 50 and 100 mg/kg induces a stimulation of the mucous secretion involving both the surface mucines and the mucines coming from antral secretion.

Compound No. 11, at dosages of 100 and 200 mg/kg, produces both an early and extended substantial stimulation of neutral mucine secretion. In addition, after 4 hours, a stimulant effect on acidic mucines secretion was noted.

This particularly favourable physiologic effect is accompanied by a remarkably low toxicity which allows a large range of use for most compounds. The acute toxicity of the compounds administered orally in mice is given in Table IV.

TABLE IV

| Compound n° | Dosage | Number of fatal issues (out of 10 animals) |
| --- | --- | --- |
| 1 | 1 g/kg | 0 |
| 2 | 1 g/kg | 0 |
| 7 | 1.5 g/kg | 0 |
| 8 | 2 g/kg | 0 |
| 10 | 1.5 g/kg | 0 |
| 11 | 3 g/kg | 0 |
| 12 | 1 g/kg | 0 |

The compounds of the formula I and their pharmaceutically acceptable acid addition salts are useful for the treatment of gastric or duodenal ulcers, as protecting agents against the side-effects of anti-inflammatory drugs, and as protecting agents of the mucous membrane of the digestive tract generally, in view of their mucus secretion properties.

Thus the present invention includes also within its scope therapeutic compositions comprising an antiulcerous effective amount of a compound of the formula I or a pharmaceutically acceptable acid addition said thereof, together with a pharmaceutically acceptable excipient.

The therapeutic compositions of this invention may be administered to human patients by the oral, rectal or parenteral routes, particularly in combination with a pharmaceutically acceptable excipient. They may be typically formulated as drinkable solutions, capsules, tablets, suppositories and injectable ampoules containing 50–500 mg active ingredient. The daily dosage regimen in adults may be 50–300 mg active ingredient.

Having now described my invention what I claim as new and desire to secure by Letters Patent is:

1. A compound selected from the group consisting of compounds of the formula:

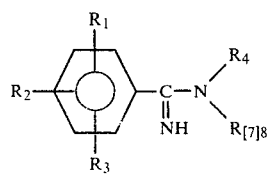

(I)

in which $R_1$, $R_2$ and $R_3$ are independently selected from one substituent selected from hydrogen, halogen, trifluoromethyl, nitro, and two $C_{1-4}$ alkoxy substituents, $R_4$ represents a heterocyclic group selected from

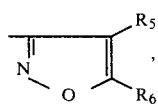

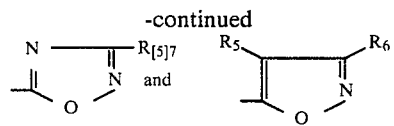

in which $R_5$ and $R_6$ are independently selected from hydrogen and methyl, $R_7$ is selected from hydrogen, $C_{1-4}$ alkyl, phenyl and halophenyl, and $R_8$ is selected from hydrogen and $C_{1-4}$ alkyl, and a pharmaceutically acceptable acid addition salt thereof.

2. 3-(Trifluoromethyl)-N-(3-phenyl-1,2,4-oxadiazol-5-yl)-benzamidine and a pharmaceutically acceptable acid addition salt thereof.

3. N-(3-phenyl-1,2,4-oxadiazol-5-yl)-benzamidine and a pharmaceutically acceptable acid addition salt thereof, 4. 4-chloro-N-(3-phenyl-1,2,4-oxadiazol-5-yl)-benzamidine and a pharmaceutically acceptable acid addition salt thereof.

5. A therapeutic composition having an activity against the human gastric or duodenal ulcers containing an antiulcerous effective amount of a compound selected from the group consisting of compounds of the formula:

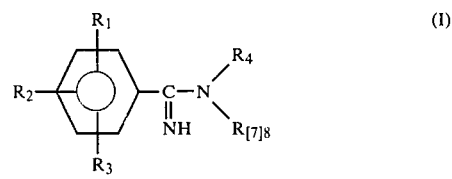

(I)

in which $R_1$, $R_2$ and $R_3$ are independently selected from one substituent selected from hydrogen, halogen, trifluoromethyl, nitro, and two $C_{1-4}$ alkoxy substituents, $R_4$ represents a heterocyclic group selected from

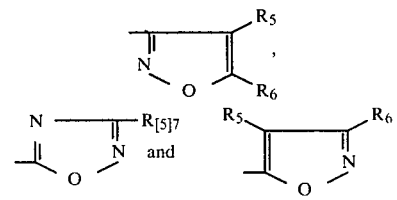

in which $R_5$ and $R_6$ are independently selected from hydrogen and methyl, $R_7$ is selected from hydrogen, $C_{1-4}$ alkyl, phenyl and halophenyl, and $R_8$ is selected from hydrogen and $C_{1-4}$ alkyl, and a pharmaceutically acceptable acid addition salt thereof, and a pharmaceutically acceptable excipient.

* * * * *